(12) United States Patent
Simonetti et al.

(10) Patent No.: US 11,026,606 B2
(45) Date of Patent: Jun. 8, 2021

(54) MAGNETIC RESONANCE IMAGING METHOD TO NON-INVASIVELY MEASURE BLOOD OXYGEN SATURATION

(71) Applicant: Ohio State Innovation Foundation, Columbus, OH (US)

(72) Inventors: Orlando P. Simonetti, Columbus, OH (US); Rizwan Ahmad, Hilliard, OH (US); Lee C. Potter, Riverlea, OH (US); Juliet Jaison Varghese, Columbus, OH (US)

(73) Assignee: OHIO STATE INNOVATION FOUNDATION

( * ) Notice: Subject to any disclaimer, the term of this patent is extended or adjusted under 35 U.S.C. 154(b) by 599 days.

(21) Appl. No.: 15/416,249

(22) Filed: Jan. 26, 2017

(65) Prior Publication Data

US 2017/0224259 A1    Aug. 10, 2017

Related U.S. Application Data

(60) Provisional application No. 62/287,116, filed on Jan. 26, 2016.

(51) Int. Cl.
| | |
|---|---|
| *A61B 5/145* | (2006.01) |
| *G01R 33/50* | (2006.01) |
| *A61B 5/055* | (2006.01) |
| *G01R 33/56* | (2006.01) |

(52) U.S. Cl.
CPC .......... *A61B 5/14542* (2013.01); *A61B 5/055* (2013.01); *G01R 33/50* (2013.01); *G01R 33/5602* (2013.01)

(58) Field of Classification Search
CPC .... A61B 5/055; A61B 5/14542; G01R 33/50; G01R 33/5602
See application file for complete search history.

(56) References Cited

U.S. PATENT DOCUMENTS

| | | | | | |
|---|---|---|---|---|---|
| 5,233,991 | A | * | 8/1993 | Wright | ................... A61B 5/055 600/410 |
| 6,904,306 | B1 | * | 6/2005 | Wu | ........................ A61B 5/055 424/9.3 |

(Continued)

OTHER PUBLICATIONS

Coolen, et al. "Quantitative T2 mapping of the mouse heart by segmented MLEV phase-cycled T2 preparation." Magnetic Resonance in Medicine 72.2 (2014): 409-417.

(Continued)

*Primary Examiner* — William J Levicky
(74) *Attorney, Agent, or Firm* — Meunier Carlin & Curfman LLC

(57) ABSTRACT

Methods for data acquisition and processing of magnetic resonance (MR) imaging to obtain the oxygen saturation (O2sat) of blood using a relationship between transverse relaxation time (T2) of blood and oxygen saturation. The method includes obtaining multiple images at various T2 preparation times. Next, non-linear curve fitting may be used to solve for arterial or venous O2sat. The disclosure provides a calibration-free method for accurate quantitative assessment of blood in the heart and deep vessels, even in locations having limited accessibility with other diagnostic techniques.

17 Claims, 10 Drawing Sheets
(6 of 10 Drawing Sheet(s) Filed in Color)

(56) References Cited

U.S. PATENT DOCUMENTS

| | | | | |
|---|---|---|---|---|
| 2005/0107681 A1* | 5/2005 | Griffiths | ............... | A61B 5/055 600/410 |
| 2012/0283549 A1* | 11/2012 | Miyazaki | ............... | A61B 5/055 600/413 |
| 2013/0088227 A1* | 4/2013 | Wernik | ............... | G01R 33/50 324/309 |
| 2015/0309137 A1* | 10/2015 | Bydder | ............... | A61B 5/055 324/309 |

OTHER PUBLICATIONS

Sun, et al. "Reduced Fetal Cerebral Oxygen Consumption Is Associated With Smaller Brain Size in Fetuses With Congenital HeartDisease." Circulation (2015):1313-1323.

Stefanovic, et al., "Human whole-blood relaxometry at 1.5T: Assessment of diffusion and exchange models". Magn Reson Med (2004), 52: 716-723. doi: 10.1002/mrm.20218.

Wedegärtner, et al., "In vivo MRI measurement of fetal blood oxygen saturation in cardiac ventricles of fetal sheep: A feasibility study". Magn Reson Med, 64: 32-41. doi: 10.1002/mrm.22344.

* cited by examiner

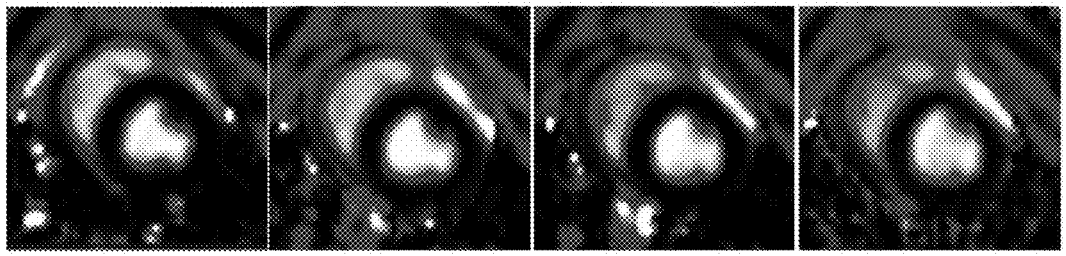
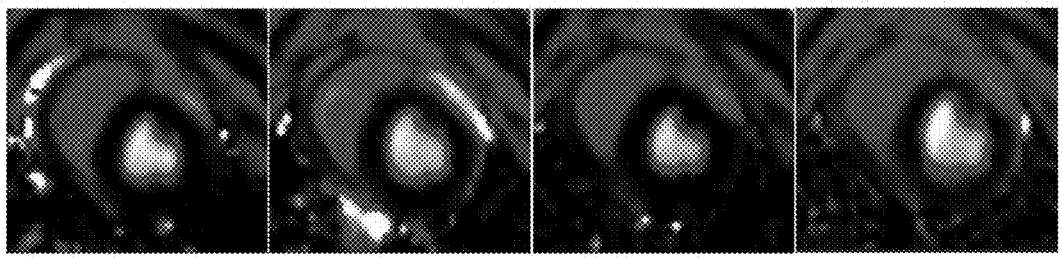
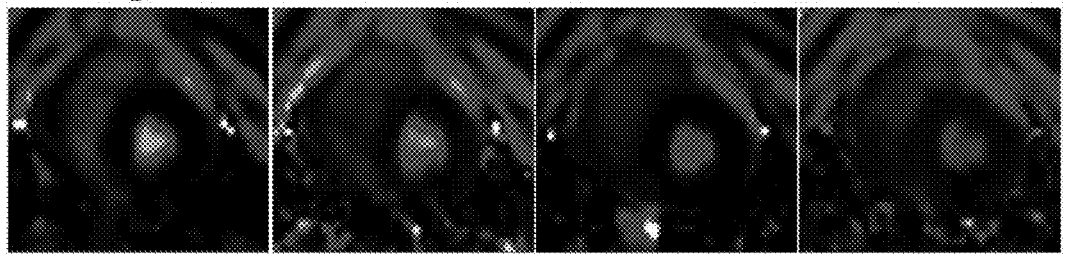
*FIG. 14*

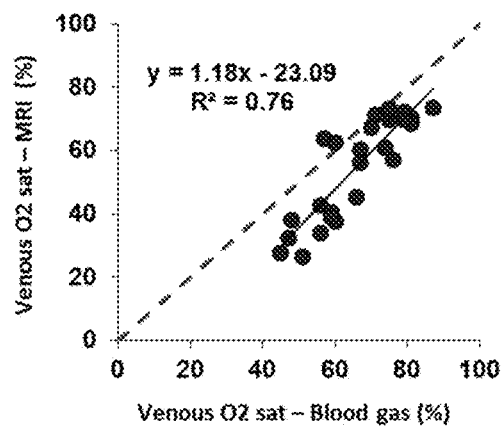
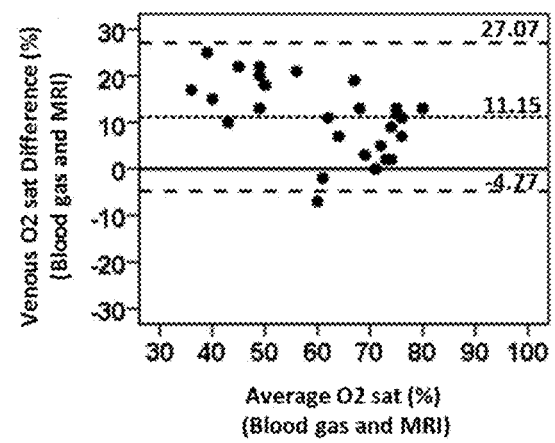
*FIG. 16A*  *FIG. 16B*
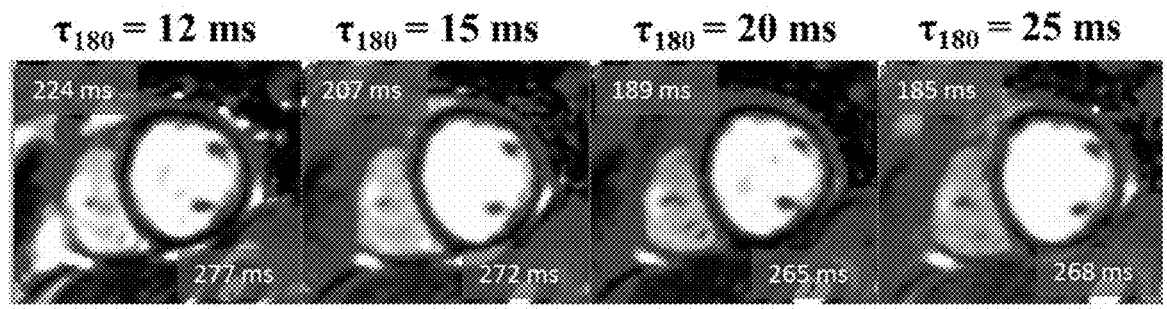
*FIG. 17*

MAGNETIC RESONANCE IMAGING METHOD TO NON-INVASIVELY MEASURE BLOOD OXYGEN SATURATION

CROSS-REFERENCE TO RELATED APPLICATION

This application claims priority to U.S. Provisional Patent Application No. 62/287,116, filed Jan. 26, 2016, entitled "MAGNETIC RESONANCE IMAGING METHOD TO NON-INVASIVELY MEASURE BLOOD OXYGEN SATURATION," which is incorporated herein by reference in its entirety.

BACKGROUND

Blood oxygen saturation (O2sat) is a relevant biomarker in a variety of cardiovascular diseases; O2sat is used to determine the presence and severity of intra- and extra-cardiac shunts in congenital heart disease and to provide an index of systemic oxygen delivery and consumption in heart failure and pulmonary hypertension. Catheterization is required to measure O2sat within the cardiac chambers, the pulmonary arteries, the vena cavae, and other deep vessels; however, this procedure is expensive, invasive, and carries associated risks. In the blood, it is known that magnetic resonance (MR) relaxation times, T1, T2 and T2* of blood may be influenced by a number of physiological, dynamic, and pulse sequence dependent factors. It is also known that the transverse relaxivity (R2 or 1/T2) of blood is related to the oxygen saturation of hemoglobin, based on the differences in magnetic properties of oxygenated (diamagnetic) and deoxygenated (paramagnetic) hemoglobin. The Luz-Meiboom (L-M) chemical exchange model has been used to mathematically characterize the relation between T2 of whole blood and its O2sat. The model describes the transverse decay that results from the transfer of protons between a protein and a water solution, and the dependence of the measured spin echo decay on the inter-echo spacing of a Carr-Purcell Meiboom Gill (CPMG) sequence. It has been applied to define the apparent 1/T2 of whole blood as the sum of the inherent and proton exchange-dependent relaxation rates of red blood cells (RBC) that contain the hemoglobin that binds oxygen, and plasma, when measured by a CPMG refocusing pulse train.

Efforts to accurately characterize this relationship between T2 and O2sat of whole blood have led to experimental and theoretical parameterization of the L-M model with varying degrees of model complexity, including segregating the contributions from individual paramagnetic and diamagnetic blood components. Wright et al was the first to quantitatively estimate blood oxygen saturation from an in vivo measurement of blood T2. They described the L-M model as $$\frac{1}{T_{2b}} = \frac{1}{T_{2O}} + (Hct)(1-Hct)\tau_{ex}\left[\left(1-\frac{\%\,SbO_2}{100}\right)\alpha\omega_0\right]^2 \times \left(1 - \frac{2\tau_{ex}}{\tau_{180}}\tanh\frac{\tau_{180}}{2\tau_{ex}}\right), \quad (1)$$

where $T_{2b}$ is the T2 relaxation time of blood (arterial or venous), $T_{2O}$ is the T2 of fully oxygenated blood, Hct is the hematocrit fraction, $\tau_{ex}$ is the water proton exchange time between erythrocytes and plasma, $\alpha$ is a dimensionless parameter that is dependent on the susceptibility difference of deoxy- and oxyhemoglobin, $\omega_0$ is the proton resonance frequency (fixed for a given static field strength), % $SbO_2$ is the oxygen saturation (arterial or venous), and $\tau_{180}$ is the inter-echo spacing of the 180° refocusing pulses in the CPMG echo train. The term $$\alpha\omega_0\left(1 - \frac{\%\,SbO_2}{100}\right)$$

represents the frequency difference between the protons in erythrocytes and plasma.

In this model, there are several unknown biophysical parameters besides O2sat that are experimentally difficult to determine. In vitro studies have been performed using static or flowing human or animal blood in order to determine these unknown parameters; however, the accuracy of estimation is prone to variability in experimental conditions. It is also unclear whether these biophysical parameters may be different under dynamic in-vivo conditions, across species, or between healthy and diseased individuals. Nevertheless, previous MRI-based approaches to determine O2sat from T2 measurements have typically relied on either assigning values to these unknown model parameters based on published data, or performing separate in vitro calibration to estimate the values of these unknown parameters.

These parameters are typically calibrated for specific imaging conditions, such as for a particular inter-echo spacing or field strength. A commonly used simplified model, initially proposed by Wright et al, is:

$$\frac{1}{T_{2b}} = \frac{1}{T_{2O}} + K\left[\left(1 - \frac{\%\,SbO_2}{100}\right)\right]^2, \quad (2)$$

where $T_{2b}$ is the measured T2 value of blood; $T_{2O}$ is the T2 value of fully oxygenated blood, which is either assumed or measured in vitro; K is a single composite calibration factor derived from in vitro experiments, containing parameters such as Hct, $\tau_{ex}$, a and $\tau_{180}$; and % $SbO_2$ is the parameter of interest, i.e. the blood O2sat. While the use of a simplified model with a fixed calibration factor may offer greater computational ease, it comes at the cost of reduced accuracy and precision. As an example, due to the dependence of K on hematocrit, the calibrated factor from an in vitro calibration process performed over a normal range of hematocrit may not be accurate in anemic or polycythemic patients. To overcome the inaccuracies of a globally calibrated model, patient-specific calibration has also been proposed. However, this process requires a significant blood draw, and in vitro oxygenation and imaging of blood samples for each individual patient. The processes of image acquisition, calibration, and off-line processing is time-consuming and has hindered widespread clinical application of previously described oximetry techniques.

Therefore, for successful clinical application in the evaluation of cardiovascular disease, T2-based MR oximetry should (i) reliably and accurately measure blood T2 in the heart and deep vessels, (ii) provide a patient-specific estimate of O2sat by accounting for inter-individual variability of the other biophysical parameters in the L-M model, and (iii) utilize a procedure for data acquisition and analysis that is clinically practical.

SUMMARY

The present disclosure is directed to novel data acquisition and processing techniques for magnetic resonance imaging (MRI) to obtain the oxygen saturation (O2sat) of blood. In particular, the present disclosure provides for an image acquisition and data processing technique for patient-specific, calibration-free, T2-based MR oximetry by, e.g., (i) measuring blood T2 in the cardiac chambers using T2 weighted MR images optimized for blood, and (ii) developing and implementing a practical approach to obtain patient-specific estimates of O2sat from blood T2. The technique has been validated against invasive blood gas analysis in a porcine model of graded hypoxemia.

The techniques of the present disclosure allow the extraction of O2sat from MR images of blood, based on the relationship between transverse relaxation time (T2) and oxygen saturation of blood. The techniques provide accurate quantitative assessment of blood O2sat in the heart and deep vessels, even in locations having limited accessibility with other diagnostic techniques. The same methodologies may also be extended to extremity vessels to evaluate limb ischemia and to the coronary sinus to evaluate myocardial energetics.

Herein, systems and methods are described that may utilize multiple T2 weighted MR images and that provide for direct measurement of easily accessible patient-specific parameters. In accordance with the implementations described in the present disclosure, multiple T2 maps may be derived from multiple T2 weighted source images with distinct preparation pulse timings. Alternatively, O2sat can be estimated directly from the T2 weighted source images. These measurements and estimates support non-linear parameter estimation resulting in accurate quantitative assessment of blood O2sat in the heart and deep vessels, even in locations having limited accessibility with other diagnostic techniques. Ranges for acquisition parameters echo time (TE) and inter-echo/pulse time/spacing ($\tau_{180}$) are selected to support non-linear parameter estimation without significant error caused by flow-induced de-phasing.

In accordance with a method of the present disclosure, oxygen saturation (O2sat) of blood is measured using magnetic resonance (MR) image data by acquiring multiple transverse relaxation time (T2) prepared source images, each of the T2 source images having distinct pulse timing; deriving multiple T2-maps from the T2 prepared source images; and using a chemical exchange model and applying a non-linear curve fitting to the multiple T2-maps to determine arterial or venous O2sat.

In accordance with another method of the present disclosure, oxygen saturation (O2sat) of blood may be determined using magnetic resonance (MR) image data from multiple transverse relaxation time (T2) prepared source images, with each of the T2 source images having distinct pulse timing; and directly using the source images, where the signal is related to T2 via an exponential function, in a chemical exchange model and applying a non-linear curve fitting to determine venous O2sat.

In the methods, the T2 prepared source images may be obtained by varying a combination of a number of refocusing pulses and $\tau_{180}$ values. In non-limiting example, the refocusing pulses range from 2 to 12 for each T2 map, and where the $\tau_{180}$ values range from 7.5 ms to 25 ms. To further improve accuracy, arterial O2sat may be measured using non-invasive pulse oximetry during the acquisition of MR data.

Thus, as will be understood, the non-invasive systems and methods of the present disclosure can be applied to quickly and accurately measure O2sat in the main pulmonary artery, the cardiac chambers, and potentially any vessel in the body, and thus, would not only reduce the need for diagnostic invasive catheterization procedures, but would also provide important physiological information that may be otherwise unavailable or unobtainable.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and/or other aspects will become more apparent by describing certain exemplary embodiments with reference to the accompanying drawings.

FIG. 14 illustrates the T2 maps acquired in a single animal at four different stages of hypoxemia where each row shows the T2 maps acquired at different $\tau_{180}$;

FIGS. 16A-B illustrate the correlation and Bland Altman plots from the evaluation of the animal data, without using a reference blood T2 and O2sat measurement for the estimation of venous O2sat, as an example embodiment; and FIG. 17 illustrates the quantitative T2 maps, each acquired at a different $T_{180}$, in a patient with cardiovascular disease.

DETAILED DESCRIPTION

Figure 1:
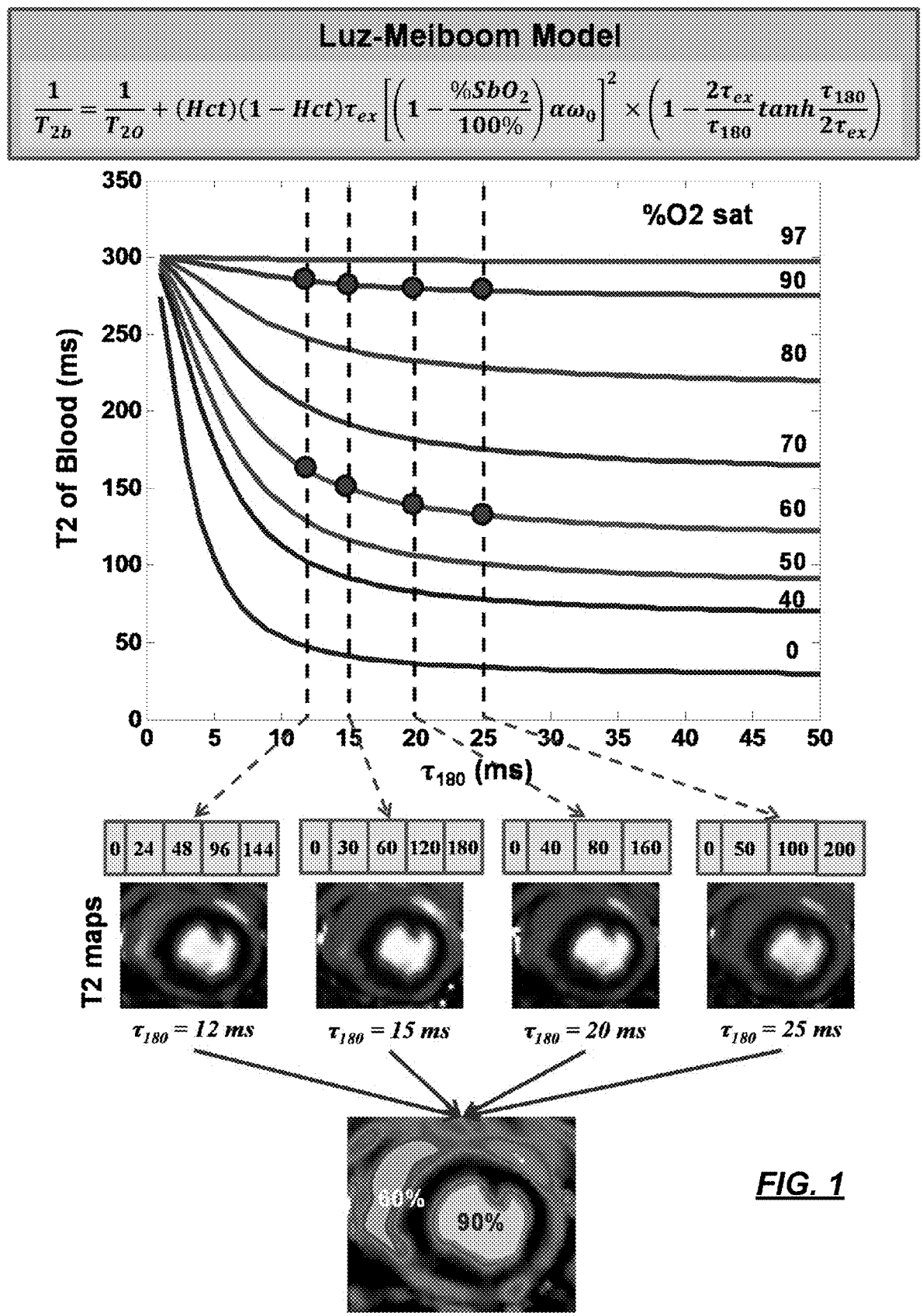
FIG. 1 illustrates the relationship between effective T2, O2sat, and $\tau_{180}$, and also provides an overview of the MR image acquisition and data processing technique to determine blood O2sat from T2.

Reference will now be made to exemplary embodiments described with reference to the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description.

Overview of Method for Clinical Utilization of MRI to Determine Blood Oximetry

In the model described in Eq. 1, $T_{2b}$ can be measured using MRI, and Hct can be measured from a small blood sample. Other parameters such as $\omega_0$ and $\tau_{180}$ can be controlled based on the choice of magnetic field strength and T2-preparation pulse design, respectively. This leaves the desired parameter, blood oxygen saturation, % $SbO_2$ and three other nuisance parameters ($T_{2O}$, $\tau_{ex}$ and $\alpha$) as unknowns.

While a single measurement of the apparent blood T2 would not be sufficient to estimate all of the unknown patient-specific parameters in the L-M model, the present disclosure provides for a method that allows these unknown parameters to be estimated on a patient-specific basis. Noting that $\tau_{180}$ is a controllable parameter, acquiring multiple T2 measurements, each at a different $\tau_{180}$, provides the diversity of data that is needed to characterize the patient-specific relationship between blood T2 and O2sat. Once a sufficient number of effective T2 weighted images have been acquired (from which quantitative T2 maps can be created as an intermediate step in the analysis, each using a different $\tau_{180}$, the four unknown model parameters (% $SbO_2$, $T_{2O}$, $\tau_{ex}$, and $\alpha$) can be stably estimated using a constrained non-linear least squares curve fit. Although the solution remains viable when the nuisance parameters are unknown a priori, a constrained model is used in order to avoid the possibility of convergence to any local minima, and thereby improve accuracy. This approach provides a framework for patient-specific, calibration-free T2 oximetry (shown in FIG. 1), and eliminates reliance on generic and often inaccurate calibration factors.

Using a technique to perform rapid, quantitative characterization of the myocardial T2 to identify inflammation and edema, $\tau_{180}$, was adjusted among four refocusing pulses in the T2 preparation train in order to vary the echo times, T2p, which is defined as T2p=number of refocusing pulses×$T_{180}$. For the estimation of blood O2sat, T2p is extended by increasing the number of refocusing pulses based on a segmented Malcolm Levitt phase cycling pattern (0, 2, 4, 8 and 12 refocusing pulses). Thus, four T2 maps may be generated for a given blood pool, using $\tau_{180}$ values of 12, 15, 20, and 25 ms. Therefore, the T2p times corresponding to each T2 map used in the study were 0, 24, 48, 96 and 144 ms (for $\tau_{180}$=12 ms); 0, 30, 60, 90 and 180 ms (for $\tau_{180}$=15 ms); 0, 40, 80 and 160 ms (for $\tau_{180}$=20 ms); and 0, 50, 100 and 200 ms (for $\tau_{180}$=25 ms), respectively.

As the MR imaging planes of the heart usually include both arterial and venous blood pools, each T2 map can provide a T2 measurement of both arterial and venous blood. It is also possible to measure the O2sat of arterial blood by non-invasive pulse oximetry. Therefore, joint processing of venous and arterial blood T2 measurements, together with a known value of arterial O2sat, can provide additional information that aids in accurate parameter estimation.

FIG. 1 shows the relationship between effective T2, O2sat, and $\tau_{180}$, and illustrates that in the physiological range of venous saturation (40% to 80%), the absolute difference in T2 between different levels of % O2sat is largely maintained down to relatively low $\tau_{180}$ (<10 ms). Reduced inter-pulse spacing can potentially reduce the sensitivity to O2sat, while higher sensitivity to O2sat at higher $\tau_{180}$ can be corrupted by the de-phasing effects caused by flowing blood. In FIG. 1, predicted T2 of blood is shown as a function of O2sat and inter-pulse spacing ($\tau_{180}$).

The graph illustrated in FIG. 1 supports a conclusion that the methodology of the present disclosure obtains multiple measurements, within a range of $\tau_{180}$ having significantly reduced influence of blood flow on T2 measurements, while maintaining the necessary T2 sensitivity to deoxygenated hemoglobin. A variable number of refocusing pulses maybe used together with a distinct $\tau_{180}$ for each of the multiple T2 maps to provide the data needed for non-linear parameter estimation. Alternatively, the MR signal from the source images can be directly used to provide the data needed for non-linear parameter estimation of O2sat without the intermediate step of generating T2 maps. Further details of the graph illustrated in FIG. 1 are provided below.

Figure 2:
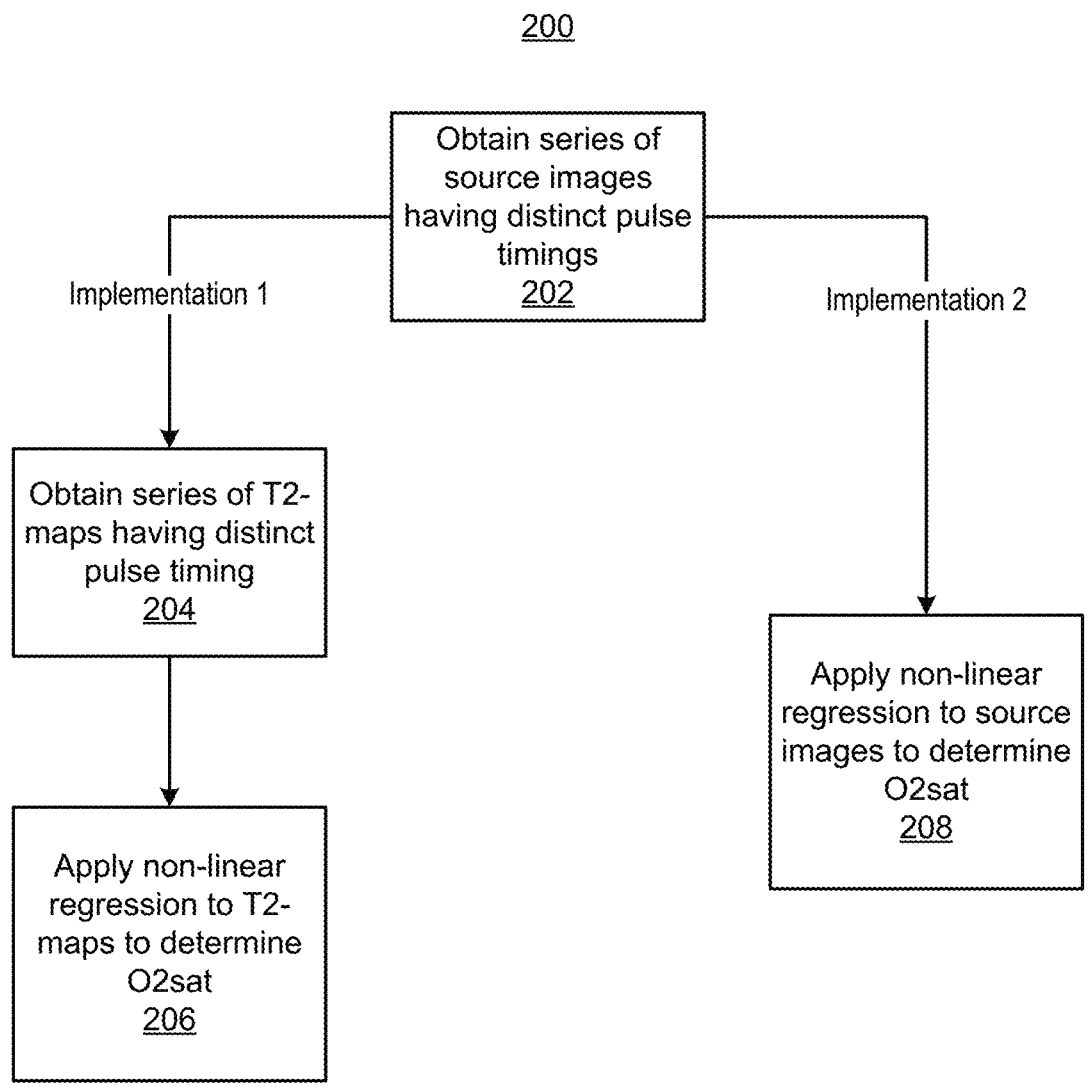
FIG. 2 illustrates an example operational flow in accordance with the present disclosure.

Implementations of Image Acquisition and Data Processing Technique to Determine Blood O2Sat With reference to FIG. 2, the present disclosure provides two implementations within an operational flow 200 for the clinical utilization of MRI to determine blood oximetry. In a first implementation (202, 204 and 206), quantitative T2-maps are utilized as an intermediate step to estimate O2sat. The first implementation begins at 202, where a series of T2-prepared balanced steady state free precession (SSFP) source images are obtained that each have distinct pulse timings. It is noted that other pulse sequences can be used, such as spoiled gradient echo, turbo spin echo (TSE) and echo planar imaging (EPI). At 204, a T2-prepared steady state free precession (SSFP) technique is used that has been successfully applied to myocardial T2 mapping. This technique takes advantage of the speed and high signal-to-noise ratio of SSFP, and incorporates automatic motion correction and in-line map generation for immediate quantitative evaluation of T2.

Figure 3:
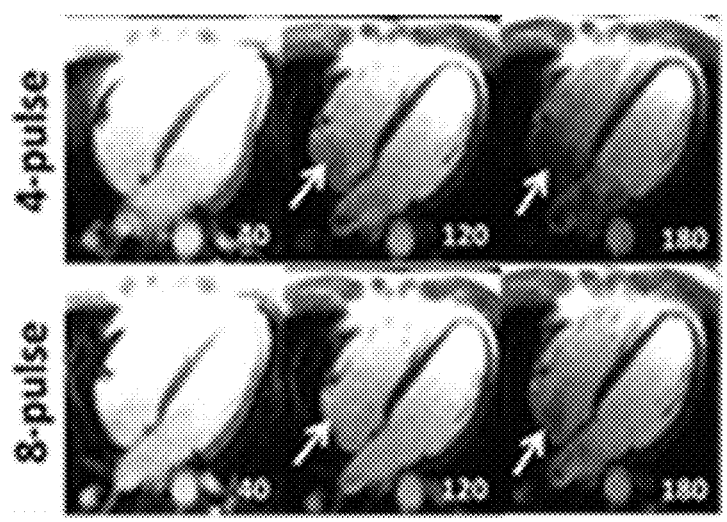
FIG. 3 illustrates example images of the right heart (venous blood) and left heart (arterial blood) at T2 preparation times of 40, 120 and 180 ms with a 4-pulse preparation scheme and an 8-pulse preparation scheme.

With reference to FIG. 3, there are example images at T2 preparation times of 40, 120 and 180 ms. Corresponding $\tau_{180}$ times for the 4-pulse images (having four T2 preparation pulses each) are 10, 30 and 45 ms, respectively, while $\tau_{180}$ times for 8-pulse images (having eight T2 preparation pulses each) are 5, 15 and 22.5 ms, respectively. Reduced flow dephasing is seen with the 8-pulse prep, which reduces $\tau_{180}$ by one-half relative to the 4-pulse prep, as shown by the white arrows. For accurate T2 mapping of flowing blood, flow artifacts may be substantially avoided if $\tau_{180}$ is as short as possible. Thus, FIG. 3 illustrates significantly reduced sensitivity to flow dephasing at shorter $\tau_{180s}$, enabling rapid and accurate quantification of T2 in the heart and deep vessels. Therefore, at 204, multiple T2 maps of blood are acquired, each map having a different $\tau_{180}$, and the range of $\tau_{180}$ being restricted to a maximum of 25 ms to minimize flow dephasing. The quantitative T2 mapping techniques will be used to generate single slice maps (images in which pixel value reflects T2) in the chambers of the heart and blood vessels in the chest.

Referring again to FIG. 2, at 206, non-linear curve fitting may be used to solve for venous O2sat. Collecting multiple T2maps with distinct pulse timing effectively generates the diversity of data needed to apply non-linear curve fitting to the L-M exchange model to estimate O2sat. Incorporating patient-specific measurements of easily accessible hematocrit and arterial O2sat, an accurate estimate of a target parameter, venous O2sat, can be obtained without the need for patient specific calibration.

In a second implementation (202, 208), the method may be performed without the intermediate step of generating a T2 map. Thus, in the second implementation, 202 is followed by 208, where the Luz-Meiboom (L-M) exchange model may be directly applied to the MR signal in the measured T2 prepared source images and a non-linear curve fitting may be used to solve for venous O2sat.

Thus, in each implementation, by addressing the flow sensitivity of the T2 preparation pulse and the inaccuracies introduced by oversimplification of the model relating T2 to O2sat, the level of accuracy and reproducibility for this technique will be raised to a level required for clinical application in cardiac patients. Further, the methodology of the present disclosure can be easily incorporated into current MRI scanning protocols for acquired and inherited heart disease to provide additional useful and practical diagnostic information.

Further details of each of steps 204, 206 and 208 are provided below.

Optimization of the T2-Preparation Pulse Timing (204)

With the above overview as an introduction to the present disclosure, optimization of the T2-preparation pulse timing will now be described. The standard T2 preparation utilized for myocardial and blood T2 mapping uses four refocusing pulses and $\tau_{180}$ up to 50 ms to achieve the longer echo times needed for blood T2 quantification. Such wide pulse spacing increases sensitivity to higher orders of motion (e.g., acceleration) and diffusion, and leads to heterogeneity and signal loss in the blood pool. While there are no gradients applied during this non-selective preparation, dephasing results from flow in the presence of local susceptibility gradients.

In accordance with the present disclosure, $\tau_{180}$ is reduced to a relatively short spacing (e.g., 25 ms or less) in order to reduce sensitivity to flow. In an example embodiment, multiple T2 maps are formed, each with a different $\tau_{180}$. The source images that are used to generate these maps use distinct numbers of refocusing pulses, including, but not limited to, 2, 4, 8, 12 pulses. In one non-limiting embodiment, the number of refocusing pulses in the source images of a single T2 map is doubled from the standard four to eight, thereby reducing the maximum $\tau_{180}$ from 50 ms to 25 ms. As such, signal loss due to flow and diffusion is reduced.

Figure 4:
FIG. 4 illustrates quantitative T2 maps of the cardiac chambers acquired in a volunteer with a 4-pulse and modified 8-pulse T2 preparation schemes.

The accuracy of T2 measured using the reduced $\tau_{180}$ prep was verified against the gold standard spin echo technique in a static phantom to have less than 10% error. Preliminary studies in a cohort of eight healthy volunteers showed the effectiveness of shortening $\tau_{180}$ in reducing blood pool variability caused by flow, as shown in FIG. 4, which illustrates quantitative T2 maps acquired in a volunteer (4-chamber view) with the standard 4-pulse (left image) and modified 8-pulse (right image) T2 preparation schemes. Note the signal homogeneity (T2) in cardiac chambers, and marked difference between venous and arterial blood with the 8-pulse prep on the right in which the pulse spacing was cut in half relative to the 4-pulse prep.

Figure 5:
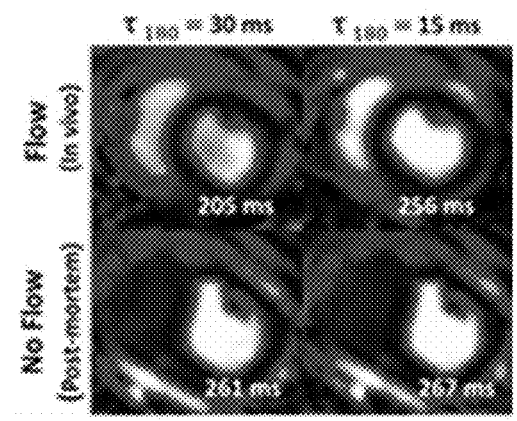
FIG. 5 illustrates in vivo pre (top row) and post mortem (bottom row) T2 maps at different average inter-pulse spacing from a pig showing the effects of flow sensitivity.

Shortening the average $\tau_{180}$ from 30 ms to 15 ms reduced the coefficient of variation in T2 measured in the right ventricle by 34%, and in the left ventricle by 60% in a cohort of healthy volunteers. Additional evidence that the modified T2 prep produces equivalent results with or without flow is shown in FIG. 5. In FIG. 5, the top row shows in vivo and the bottom row shows immediate post mortem T2 maps from a pig showing flow sensitivity at longer $\tau_{180}$ (upper left), which artificially shortens the T2 in the left ventricle blood pool, while T2s acquired at shorter $\tau_{180}$ (right) are within 4% with or without flow. Thus, the maps acquired in a pig immediately pre- and post mortem, at the same invasively measured arterial O2sat (100%), show minimal effect of flow on T2 measured using the shortened $\tau_{180}$ prep. Using this knowledge, in accordance with the first implementation of FIG. 2, multiple T2 maps may be acquired where each map is composed of several different source images, and each T2 map at a specific $\tau_{180}$. The source images in a specific T2 map will, for example, utilize preparation pulses ranging from 2 to 12 to keep the $\tau_{180}$ at a constant value for a given T2 map.

Non-Linear Parameter Estimation (206)

The Luz-Meiboom (L-M) model is widely accepted as a valid description of the mechanism of T2 relaxation facilitated by proton exchange between sites at two different resonant frequencies. The L-M model equates the reciprocal of the T2 relaxation to a sum of two terms: the reciprocal of the relaxation time of blood at 100% oxygen saturation and a term proportional to $(1-O2sat)^2$. The proportionality constant for the second term depends on five physical parameters: the hematocrit (Hct), or volume ratio of red blood cells (RBC) to the total volume of blood; the proton exchange time ($\tau_{ex}$); a dimensionless parameter, alpha ($\alpha$), related to the magnetic susceptibility of deoxyhemoglobin; the proton resonance frequency ($\omega_0$); and the 180° pulse interval of a spin echo or T2 preparation train ($\tau_{180}$). The pulse interval and resonance frequency are under experimental control. Other unknown parameters are considered nuisance parameters, and importantly, may vary from individual to individual. At a given field strength (where $\omega_0$ is fixed), by manipulating the pulse interval, multiple T2 maps are generated in both venous and arterial blood pools; in this manner, the quantity of interest, blood O2sat, and all unknown nuisance parameters may be jointly estimated, bypassing the existing need for technique or patient-specific in vitro calibration.

With regard to the L-M model specified in Eq. 1, it has a number of parameters that are either controlled or calibrated. A common practice is to lump the calibration parameters into two composite calibration parameters, $T_{2O}$ and a constant, K, defined by Wright et al. as:

$$K = Hct(1 - Hct)\alpha^2 \omega_0^2 \tau_{ex}\left(1 - \frac{2\tau_{ex}}{\tau_{180}}\tanh\left(\frac{\tau_{180}}{2\tau_{ex}}\right)\right), \quad (3)$$

which has units $ms^{-1}$ or $s^{-1}$. K lumps together parameters that depend on the scanning conditions ($\tau_{180}$ and $\omega_0$) with other parameters that depend on patient-specific characteristics of the blood (Hct, $\tau_{ex}$, and $\alpha$). Substituting K into the L-M model results in the simplified equation proposed by Wright et al., which was introduced above:

$$\frac{1}{T_{2b}} = \frac{1}{T_{2O}} + K\left(1 - \frac{\% SbO_2}{100}\right)^2 \quad (4)$$

While computationally the simplest, this model does not take into account the effect of individual hematocrit, nor the inter-individual variation in the other biophysical parameters, $\tau_{ex}$, and $\alpha$, and could lead to inaccurate estimation of O2sat in patients with abnormal hematocrit levels. Wright et al. also observed a dependence of Hct on the constant term, $T_{2O}$. Since then, a more comprehensive theoretical model, incorporating patient specific hematocrit, has been proposed by Golay et al.

$$\frac{1}{T_{2b}} = \frac{1}{T_{2p}} + Hct\left[(R2_{dia} + R2_{oxy}) + \left(1 - \frac{\% SbO_2}{100}\right)(R2_{deoxy} - R2_{oxy})\right] + \quad (5)$$

$$(Hct)(1 - Hct)\tau_{ex}\left[(\omega_{dia} + \omega_{oxy}) + \left(1 - \frac{\% SbO_2}{100}\right)(\omega_{deoxy} - \omega_{oxy})\right]^2 \times$$

$$\left(1 - \frac{2\tau_{ex}}{\tau_{180}}\tanh\frac{\tau_{180}}{2\tau_{ex}}\right)$$

The additional parameters from Eq. 1 being the relaxation time of plasma ($T_{2p}$), the relaxation rates of diamagnetic blood components, oxyhemoglobin and deoxyhemoglobin ($R2_{dia}$, $R2_{oxy}$ and $R2_{deoxy}$), and the frequencies of diamagnetic blood components, oxyhemoglobin and deoxyhemoglobin ($\omega_{dia}$, $\omega_{deoxy}$ and $\omega_{oxy}$) under the influence of an external magnetic field.

These different versions of the model have been extensively used for in vitro characterization of the magnetic properties and dependence of blood T2 in both human and animal blood, and across different field strengths. The conventional approach is to generate empirically determined calibration factors for the unknown parameters in the model, which are then applied to the general population to aid in the estimation of O2sat from T2. Studies involving patient specific calibration factors have also been performed to estimate O2sat more accurately, but this still involves drawing blood samples from each individual to perform an in vitro calibration, making the whole process cumbersome and impractical.

The method for patient-specific, calibration free T2 based MR oximetry of the present disclosure has been evaluated by a controlled graded hypoxemia experiment in a porcine model across a range of oxygen saturation levels (detailed below). The performance of the method in the different versions of the L-M model with four (Eq. 1), three (Eq. 2) and six (Eq. 6) unknown parameters respectively, as defined in Eqns. 1-6, are also examined below. Examining Eqns. 1-6, the parameters of the L-M model can be either directly measured, controlled or estimated. The measurable parameters are blood T2 in the regions of interest (arterial and venous), and hematocrit, which can be measured from a small blood sample. The controllable parameters are $\omega_0$, and $\tau_{180}$, the inter-echo spacing of the T2 preparation pulses in the imaging sequence. This leaves the remaining unknown/nuisance parameters to be estimated along with % SbO2— the blood oxygen saturation. The technique described in this disclosure samples the curve that defines the T2-O2 relationship at different values of $\tau_{180}$.

As shown in the example embodiment in FIG. 1, to convert blood T2 to its corresponding O2sat, four T2 maps are acquired resulting in eight equations—four for a reference arterial blood pool and four for the venous blood of interest. These T2 measurements, together with the hematocrit and non-invasive arterial O2sat, collectively, support a reliable fit of the L-M model to accurately estimate the unknown parameters without the need for a separate calibration procedure.

Non-Linear Parameter Estimation (208)

In the second implementation, the signal from the source images is directly employed in the L-M model instead of calculating an intermediate T2 measurement. Here, determining T2 maps is not necessary as O2sat estimates can be derived directly from a series of T2-prepared images without the intermediate step of T2 estimation. Referring to the discussion above, the equation relating the signal to T2 is expressed as S=S0*exp(-TE/T2), where S is the measured signal in each source image, S0 is the initial signal, and the echo time or T2 preparation time, TE, is the product of the number of refocusing pulses and $\tau_{180}$. S0 becomes an additional nuisance parameter to be solved for. Alternatively, S0 can be treated as the signal measured in the T2 prepared image with 0 refocusing pulses.

Preliminary Implementation and Testing—Volunteer Study

Example Equipment

In this example embodiment, all MR imaging experiments are performed using a 1.5 T MRI system (MAGNETOM, Avanto, Siemens) with maximum gradient amplitude of 40 mT/m and slew rate of 200 mT/m/msec. A cohort of volunteers were additionally examined at a 3 T MRI system (Magnetom Tim Trio, Siemens).

T2 Preparation Schemes

Based on preliminary evaluation of the compromise between flow sensitivity and T2 sensitivity to oxygen saturation, in this example, the preparation pulses will utilize $\tau_{180}$ ranging from 7.5 ms up to 25 ms, with the number of refocusing pulses ranging from 2 to 12 for each T2 map. Although additional pulses increase the overall specific absorption rate (SAR) of the pulse sequence, (for example, by a factor of approximately 1.8 from 4-pulse to 8-pulse), this has not proven to be a limiting factor at 1.5 T, the field strength at which most clinical cardiac MRI is performed, for the combination of pulses and $\tau_{180}$ times mentioned above. Additionally, evaluating the sequences (T2 prepared MR images with 8 refocusing pulses and T2 maps with constant $\tau_{180}$) in seven volunteers at 3.0 T found it to be well within SAR limits (for example, 1.35±0.24 W/kg at $\tau_{180}$ of 7.5 ms for variable number of pulses up to 12).

Volunteer Study at 1.5 T

Figure 6:
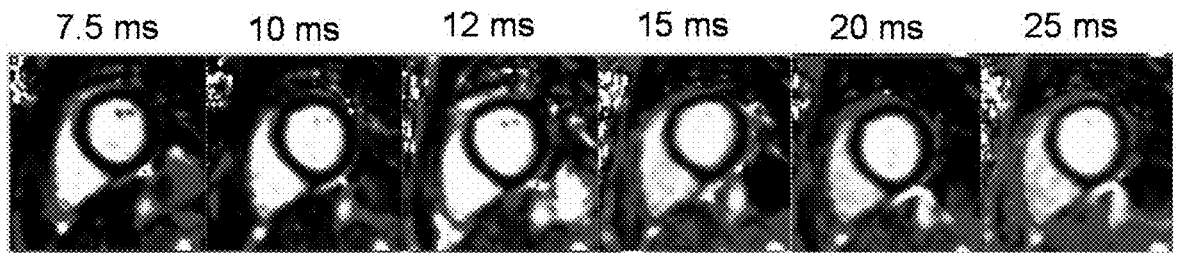
FIG. 6 illustrates images showing six different T2 maps of the right (venous blood) and left (arterial blood) ventricles, each with a fixed $\tau_{180}$ that are acquired in a volunteer at 1.5 T.

The study aimed to evaluate if the technique described in this disclosure provided estimates of O2sat within normal physiological range. The study was conducted in eleven healthy volunteers (two females, mean age 27.7±6.7 years). After obtaining written informed consent to participate in the study, a venous blood sample was drawn from the subject's arm for a measurement of the hematocrit fraction (to estimate O2sat). A three lead electrocardiogram was placed on the subject's chest in order to monitor heart rate and for cardiac triggering of MR images. A six-element phased array body coil was placed over the thorax and combined with six elements of a spine array coil for signal reception. In addition, a pulse oximeter probe was placed on the finger for monitoring arterial oxygen saturation during the acquisition of MR images. FIG. 6 illustrates images showing six different T2 maps of the right (venous blood) and left (arterial blood) ventricles, each with a fixed $\tau_{180}$ that are acquired in a volunteer at 1.5 T.

To estimate venous O2sat, four T2 maps were acquired in a short axis or horizontal long axis view of the right and left ventricles were utilized. Some of the volunteers had multiple data acquisitions (range, two to five data sets). The images were cardiac triggered and acquired free breathing during late diastole. Each T2 map was acquired using a different inter-echo spacing of 12, 15, 20 and 25 ms respectively. The other imaging parameters of the T2 maps were TR: 4000 to 5000 ms (four to six R-R intervals), one signal average, flip angle=70°, parallel acceleration=2, Bandwidth=1182 Hz/pixel, spatial resolution=2.4×2.4×10 mm. The acquisition time of each T2 map was approximately 20 to 30 seconds.

The T2 value of arterial and venous blood were measured by manually drawing contours around the lumen of the left and right ventricles in each of the T2 maps. For each volunteer, the multiple T2 measurements of the arterial and venous blood pool, along with hematocrit and non-invasive arterial O2sat were processed jointly to estimate venous oxygen saturation along with other nuisance parameters ($T_{2O}$, $\tau_{ex}$ and $\alpha$). The initial estimates and bounds for the unknown parameters were: 0.8 [0, 1] for venous O2sat, 300 [0, 400] ms for $T'_{2O}$, 3 [2, 7] ms for $\tau_{ex}$ and 0.5 [0.2, 0.6] ppm for $\alpha$. These initial estimates and constraints were kept constant for all the measurements and analysis in this volunteer study.

Figure 7:
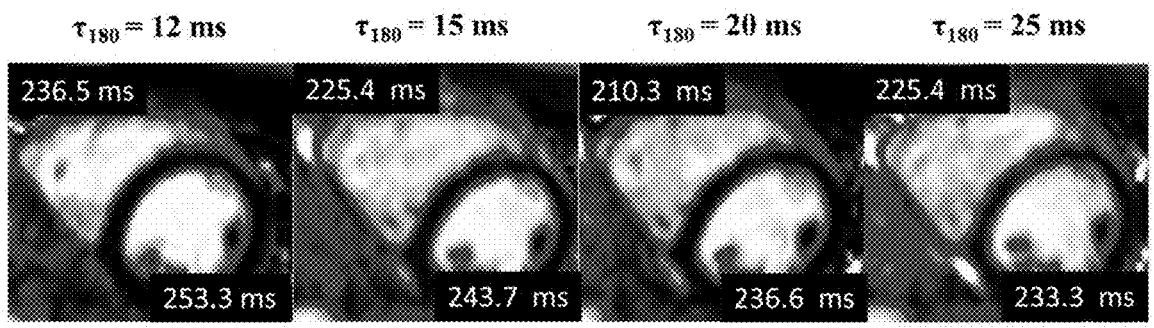
FIG. 7 illustrates images showing four different T2 maps of the right (venous blood) and left (arterial blood) ventricles, each with a fixed $\tau_{180}$ that are acquired in a volunteer at 1.5 T to generate a set of equations for the Luz-Meiboom model relating blood T2 and O2sat.

T2 maps acquired in a volunteer in a in a mid-short axis view of the ventricles at 1.5 T for six different $\tau_{180}$ are shown in FIG. 6. The four T2 maps used for analysis (at $\tau_{180}$ times of 12, 15, 20 and 25 ms) along with the measured T2 of venous (boxes on upper left) and arterial (boxes on lower right) acquired in a volunteer are also shown in FIG. 7. Of the thirty two estimates of venous O2sat in this study, twenty six measurements were estimated within the normal physiological venous O2sat range of 60% to 80%. The O2sat was estimated higher than 80% from the six other data sets. The mean, standard deviation and range of the venous O2sat and other nuisance parameters estimated from fitting the measured variables to the L-M model are shown in Table 1.

TABLE 1

| Estimated parameters | Mean ± SD | Range |
| --- | --- | --- |
| Venous O2sat (%) | 73.04 ± 7.55% | 61-89% |
| $T_{2O}$ (ms) | 245.13 ± 13.98 ms | 220.95-275.45 ms |
| $\tau_{ex}$ (ms) | 5.85 ± 1.44 ms | 3.01-6.99 ms |
| $\alpha$ (ppm) | 0.31 ± 0.07 ppm | 0.23-0.45 ppm |

In this proof of concept study, the proposed calibration-free non-invasive MR oximetry method was implemented in a preliminary cohort of healthy volunteers at 1.5 T, and venous O2sat was estimated in the right ventricle. The estimated venous O2sat in the majority of the volunteers remained within the normal range of 60% to 80%. The accuracy of the venous O2sat measurement could not be verified against any invasive reference standard in this cohort, as it is impractical to conduct a research study wherein an invasive procedure has to be performed in healthy volunteers.

Volunteer Study at 3 T

A preliminary evaluation was conducted in a cohort of healthy volunteers at 3 T magnetic field strength. Subject consent and preparation procedures were the same as the volunteer study at 1.5 T. Following the acquisition of breath held localizers to identify the mid-short axis imaging plane. Four T2 prepared SSFP quantitative T2 maps ($\tau_{180}$=10, 12, 15 and 20 ms, TR>3000 to 4000 ms, FA=40°, 2.8×2.8×10 mm³, NEX=2, free breathing) were acquired in seven volunteers (mean age: 32.6±12.2 years, four females) on a 3 T MRI system (Tim Trio, Siemens Healthineers, Erlangen, Germany). The T2p times for the maps were 0, 20, 40, 80 and 120 ms for $\tau_{180}$=10 ms, 0, 24, 48, 96 and 144 ms for $\tau_{180}$=12 ms, 0, 30, 60 and 120 ms for $\tau_{180}$=15 ms and 0, 40, 80 and 160 ms for $\tau_{180}$=20 ms. The average acquisition time for the T2 maps was approximately 40 to 60 seconds.

The T2 of venous and arterial blood were measured in each map in an ROI in the right and left ventricle. For each volunteer, the multiple T2 measurements of the arterial and venous blood were processed jointly to estimate venous O2sat along with other nuisance parameters. The values of hematocrit (Hct) and arterial O2sat were assumed at 0.41 and 0.97 respectively for all volunteers. The initial constraints and bounds for the unknown parameters were the same as used in the volunteer study at 1.5 T.

Figure 8:
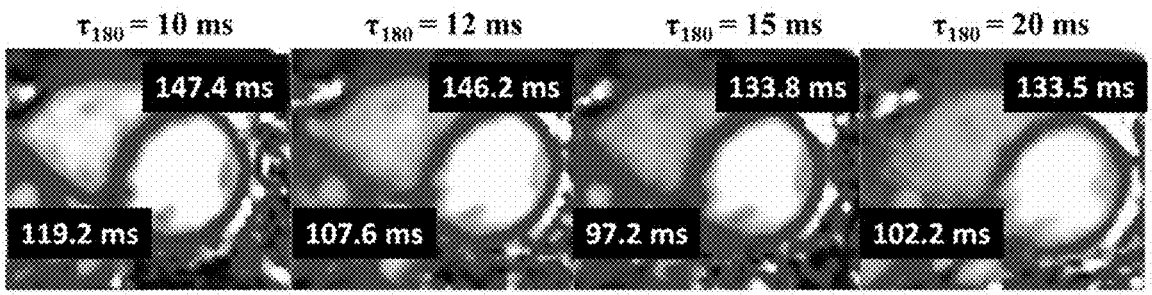
FIG. 8 illustrates images showing four different T2 maps of the right (venous blood) and left (arterial blood) ventricles, each with a fixed $\tau_{180}$ that are acquired in a volunteer at 3 T.

FIG. 8 shows the T2 maps acquired at different $\tau_{180}$ in a volunteer at 3 T. Table 2 shows the mean and standard deviation, and the range of the estimated parameters venous O2sat, $T_{2O}$, $\tau_{ex}$ and $\alpha$ in the volunteers at 3 T.

TABLE 2

| Estimated parameters | Mean ± SD | Range |
| --- | --- | --- |
| Venous O2sat (%) | 73.12 ± 4.26 | 63.80-76.26 |
| $T_{2O}$ (ms) | 149.65 ± 9.82 | 140.91-167.63 |
| $\tau_{ex}$ (ms) | 3.99 ± 1.49 | 2.0-6.51 |
| $\alpha$ (ppm) | 0.39 ± 0.07 | 0.30-0.50 |

The average venous O2sat was similar for volunteers at both field strengths. The estimated venous O2sat for all volunteers was within the normal physiological range at 3 T.

The feasibility of the proposed oximetry technique was demonstrated in a cohort of healthy volunteers at 3 T in this study. In conclusion, the volunteer studies at 1.5 T and 3 T served to implement and establish proof of the proposed concept at clinically used field strength.

Testing and Validation—Animal Hypdxemia Study

Figure 9:
FIG. 9 Illustrates additional validation of the technique of the present disclosure in an animal hypoxemia model.
Figure 10:
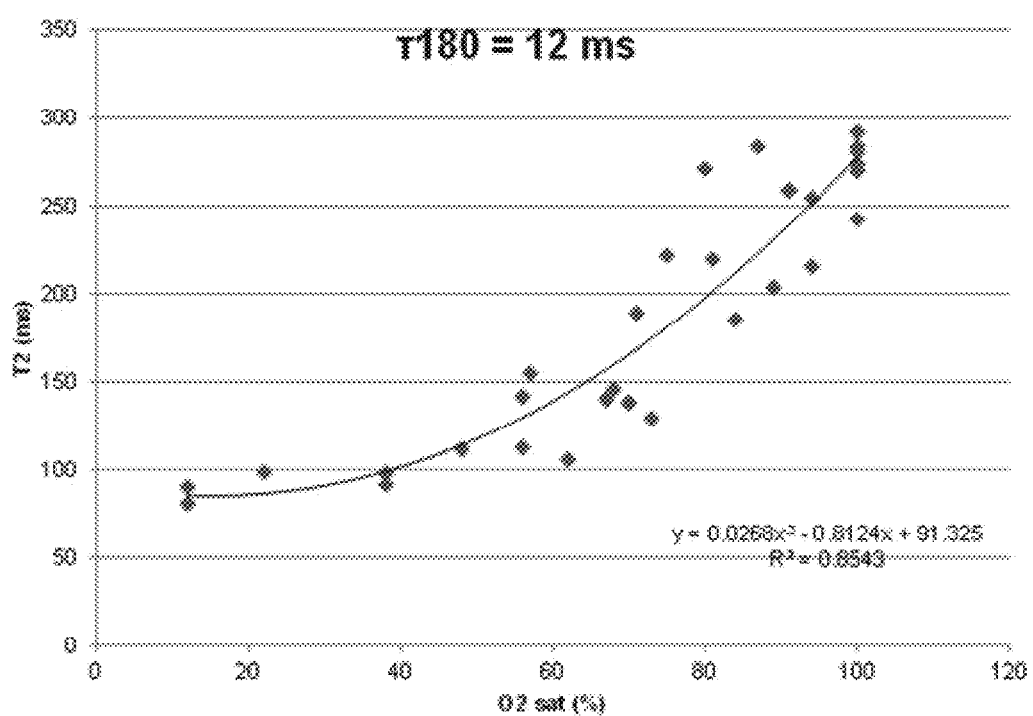
FIG. 10 shows the data from animal experiments, illustrating the non-linear relationship between T2 and O2sat at a given inter-pulse spacing ($\tau_{180}$) of 12 ms.
Figure 11:
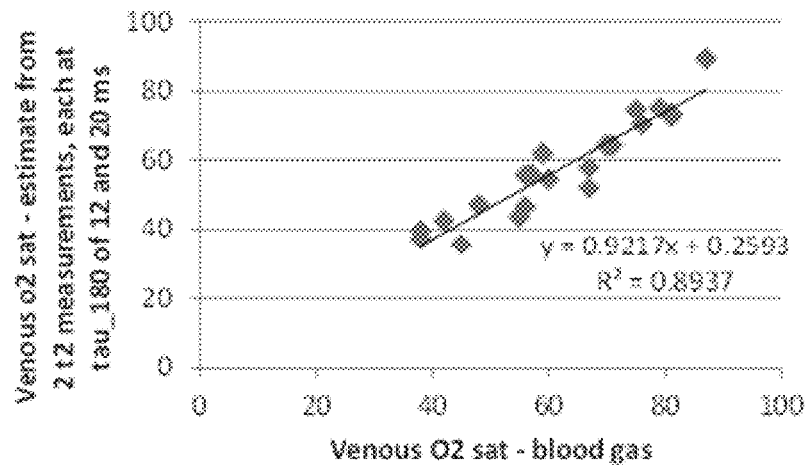
FIG. 11 illustrates a comparison of venous oxygen saturation measured from an invasive blood sample against the venous O2sat estimated from the present disclosure technique, with a minimum of two T2 maps at distinct pulse timings ($\tau_{180}$) of 12 and 20 ms.
Figure 12:
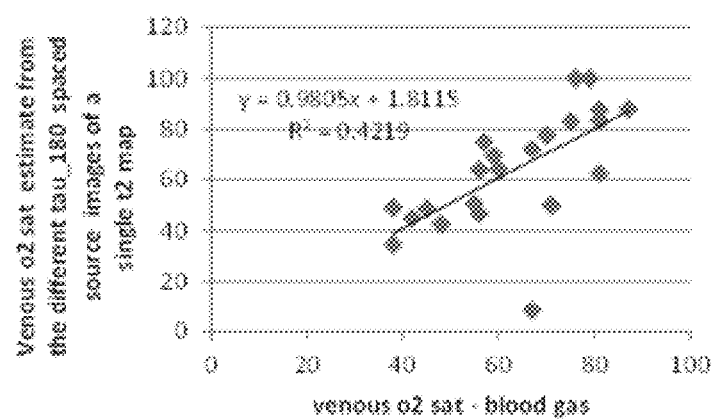
FIG. 12 illustrates additional data from animal experiments, demonstrating comparison of venous oxygen saturation measured from an invasive blood sample against the venous O2sat estimated directly from the T2 weighted source images, the alternative implementation described in (202, 208) in the present disclosure technique.
Figure 13A:
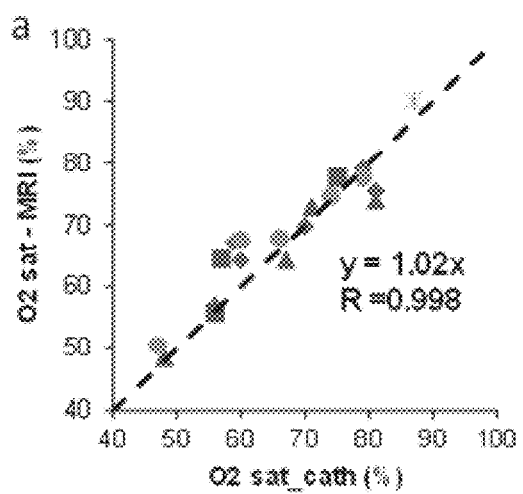
FIGS. 13A-D illustrate correlation and Bland Altman plots for the results of the animal study using the technique described in the present disclosure in comparison with the previously proposed method of applying a fixed calibration factor K.
Figure 13B:
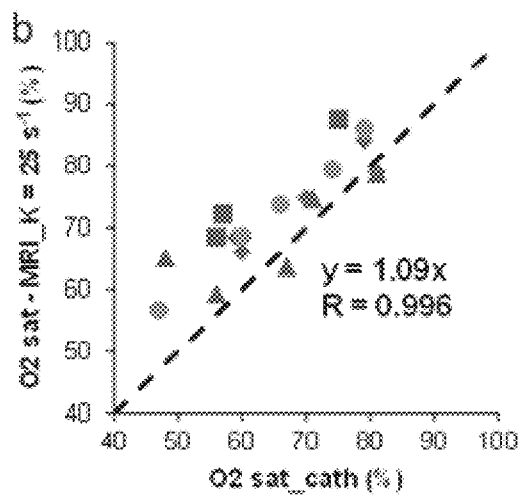
Figure 13C:
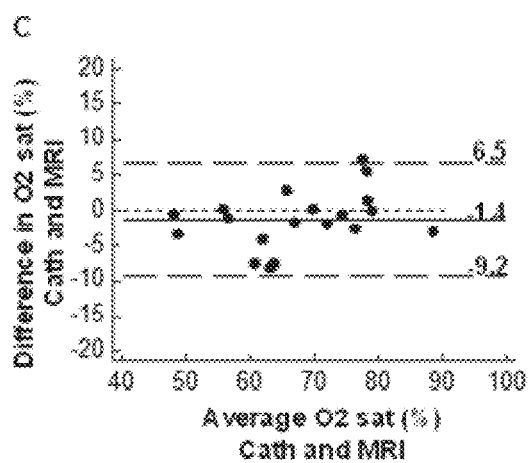
Figure 13D:
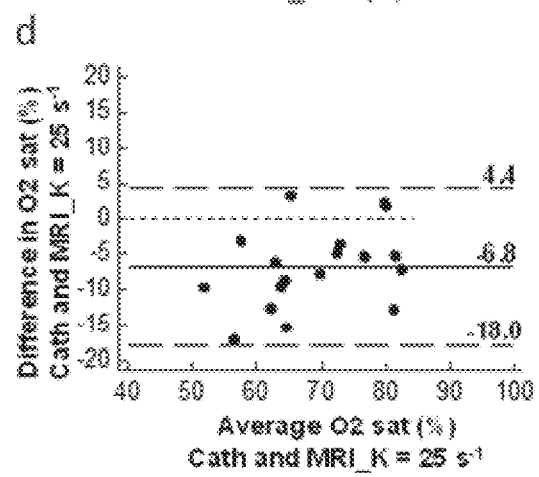

The above methodology was tested by measuring T2 at different $\tau_{180}$ in a porcine model of graded hypoxia and in healthy volunteers. With respect to the animal hypoxemia study, FIG. 9 Illustrates additional validation of the technique of the present disclosure in the animal hypoxemia model. In particular, FIG. 9 shows the oxygen saturation of arterial and venous blood was varied in these experiments. The T2 maps in FIG. 9 show that T2 measurements acquired with the technique described in this disclosure reflect change in O2sat. The values in parenthesis indicate the O2sat measured by invasive catheterization and blood gas analysis. FIG. 10 shows the data from animal experiments, illustrating the non-linear relationship between T2 and O2sat at a given inter-pulse spacing ($\tau_{180}$) of 12 ms. This highlights that the O2sat and T2 measured in blood in these studies is in accordance with the relationship between T2 and O2 sat described in Eq. (1-6). As an exemplary embodiment, FIG. 11 illustrates a comparison of venous oxygen saturation measured from an invasive blood sample against the venous O2sat estimated from the present disclosure technique, with a minimum of two T2 maps at distinct pulse timings ($\tau_{180}$) of 12 and 20 ms. As shown, the method of the present disclosure provides a slope close to 1 and offset close to 0. FIG. 12 illustrates additional data from animal experiments, demonstrating comparison of venous oxygen saturation measured from an invasive blood sample against the venous O2sat estimated directly from the T2 weighted source images, the alternative implementation described in (202, 208) in the present disclosure technique. FIGS. 13A-D illustrate that there is a very close match between the MRI-derived estimate and invasive catheter measurement of venous O2sat and also that there is improvement as compared to the previous method of applying a literature-derived value for K. These preliminary results provide confidence that the combination of rapid blood T2 measurement with T2 mapping, measuring all other easily available parameters a priori, acquiring multiple T2 measurements within a range of $\tau_{180}$ that has reduced flow sensitivity in the T2 preparation, and applying non-linear curve fitting to the L-M model can result in significant improvement in the MRI-derived estimation of venous O2sat. The details of the experiment are described below.

The study was conducted with the approval of the Institutional Animal Care and Use Committee (IACUC). Seven pigs were anesthetized with isoflurane and ventilated on 100% O2. Balloon catheters were inserted into the right atrium and proximal aorta for sampling venous and arterial blood respectively. After placement in the MR scanner, the animals were subjected to controlled graded hypoxemia by varying the ratio of oxygen to nitrogen gas inhaled. It was sought to achieve arterial O2sat levels ranging from 100% down to 70% in each animal.

Each inspired gas mixture was maintained for at least 10 minutes to allow oxygen saturation levels to stabilize before blood sampling and imaging. Arterial and venous blood samples (roughly 0.1 mL) were drawn from the aortic and right atrial catheters before and after imaging at each hypoxemic stage; the samples were immediately analyzed with a Vetscan I-stat 1 handheld blood gas analyzer (Abaxis Inc., Union City, Calif., USA). The arterial and venous O2sat for each hypoxemic stage was determined by averaging the saturation levels measured before and after imaging (approximately ten minutes apart). The hematocrit was measured in each blood sample and averaged across all measurements to determine the value for each animal.

After stepping through stages from highest to lowest level of inspired oxygen, the animal was allowed to recover for approximately 15-20 minutes by breathing 100% O2. The animal was then euthanized after a second set of measurements were made at 100% arterial O2sat.

MRI Protocol

All imaging was performed on a 1.5 T magnet (MAGNETOM Avanto, Siemens Healthineers, Erlangen, Germany) with a maximum gradient amplitude of 45 mT/m and slew rate of 200 mT/m/ms. A flexible six-element phased array body coil was placed on the thorax over the heart and combined with elements of a spine array coil for signal reception. MRI at each stage of hypoxemia included the acquisition of four T2 maps, each using a different $\tau_{180}$, in a single short axis view including both right and left ventricles. At each stage of hypoxemia, four T2 maps, each with $T_{180}$ of 12, 15, 20 and 25 ms were acquired in a randomized order to avoid any bias that may be caused by the drifting of the O2sat levels. The images were cardiac triggered and acquired free breathing in late systole to avoid rapid, disrupted flow during diastolic filling. The imaging parameters were TR: 4000 to 5000 ms (seven to fourteen cardiac cycles), two signal averages (NEX), flip angle=70°, parallel acceleration=2, bandwidth=1182 Hz/pixel, spatial resolution=2.8×2.8×10 mm. The acquisition time of each map was approximately 40 to 50 seconds. Cardiac output was measured at the aortic outflow using a real-time velocity sequence at each hypoxemia stage (TR/TE=96.4/5.1 ms, TA=5 sec, spatial resolution=3.8×3.1×10 mm). Heart rate was monitored using a 3-lead wireless electrocardiogram, and arterial oxygen saturation was monitored by placing a pulse oximeter probe on the lower lip of the animal.

Image Analysis

All image analysis was performed on a Leonardo workstation (Siemens Healthineers, Erlangen, Germany). The T2 value of arterial and venous blood were measured by manually drawing contours around the lumen of the right ventricular (venous) and left ventricular (arterial) blood pools in each of the four T2 maps acquired at each hypoxemia stage. These measurements (four arterial and four venous), along with the measured hematocrit and reference arterial O2sat at each stage were processed jointly to estimate venous O2sat along with other nuisance parameters ($T_{2O}$, $\tau_{ex}$, and $\alpha$) in the L-M model.

Parameter estimation from the L-M model was performed with a constrained non-linear least squares method using an interior point algorithm in Matlab R2016a (The Mathworks, Natick, Mass., USA). Blood T2, hematocrit, and arterial O2sat (by blood gas analysis) were all measured, and $\omega_0$ ($4 \times 10^8$ rad/s at 1.5 T) and $\tau_{180}$ (12, 15, 20 and 25 ms) were known.

The performance of the proposed MR technique was compared against the previously proposed solution of applying a global predetermined calibration factor (K=25 s$^-$) to a single T2 measurement ($\tau_{180}$=12 ms) using the simplified model in Eq. 2. There are two unknown parameters in this simplified model, $T_{2O}$ and $SbO_2$. As previously proposed by Wright et al, $T_{2O}$ was first calculated for each hypoxemia stage using the reference measurement of arterial O2sat measured in samples drawn by invasive catheterization. The calculated $T_{2O}$, predetermined K and measured venous blood T2 were then used in Eq. 2 to solve for venous O2sat.

Statistical Analysis

All variables are reported in mean±standard deviation. Statistical analysis was performed in SPSS (Version 23, IBM Corp, Armonk, N.Y., USA). Linear regression was performed to compare the relationship between the venous O2sat estimated using MRI against the reference venous O2sat measured by blood gas analysis. The bias and limits of agreement between the two methods were evaluated by the Bland Altman method. Statistical significance was inferred for $p<0.05$.

Results

Thirty three paired measurements of arterial and venous blood at different oxygen saturation levels were obtained from the seven animals. Two of the animals died during the experiment. However, there were three usable data sets (pertaining to inhalation conditions/hypoxemia stages) in one of these animals and one usable data set in the other; these were used in the analysis. Six data sets, where the venous O2sat fell below 40% were excluded from the analysis since rapid breathing, along with high and variable heart rates at these severe hypoxemia stages significantly degraded image quality. Therefore, the data used in the final analysis included twenty seven measurements—from one hypoxemia stage in one animal, three hypoxemia stages in two animals, and five hypoxemia stages in the other four animals.

Using exhaustive search, a set of bounds that minimized average absolute error in estimated venous O2sat was chosen. These bounds (listed in Table 3) acted as constraints for non-linear least squares curve fitting of the remaining 19 data sets. These bounds limit the solution space and thus avoid local minima or physiologically improbable values.

TABLE 3

| Estimated Parameters | Initial Value | Constraints |
|---|---|---|
| % SbO$_2$ | 0.8 | [0-1] |
| T$_{2O}$ (ms) | 300 | [200-400] |
| τ$_{ex}$ (ms) | 3 | [0-6] |
| α (ppm) | 0.545 | [0.52-0.57] |

The average baseline characteristics for all animals are listed in Table 4. The mean hematocrit fraction in all animals was 0.25±0.03 (range, 0.20 to 0.29). For the training set, the venous O2sat levels measured by catheter sampling ranged from 45% to 81%; for the testing set, the venous O2sat ranged from 47% to 87%.

TABLE 4

| Baseline Characteristics | Mean ± SD |
|---|---|
| Heart Rate (bpm) | 97 ± 18 |
| Cardiac output (L/min) | 5.42 ± 0.97 |
| Arterial blood pH | 7.45 ± 0.05 |
| Venous blood pH | 7.39 ± 0.05 |
| Arterial pO2 (mmHg) | 511.86 ± 17.53 |
| Venous pO2 (mmHg) | 44.64 ± 5.23 |

The heart rate and cardiac output increased with progressive hypoxemia in all animals. Arterial and venous blood T2 values decreased with lower levels of inspired O2. T2 measurements of arterial and venous blood generally decreased with increasing τ$_{180}$. The T2 maps acquired at four different stages of hypoxemia in one animal are shown in FIG. 14. Each row of FIG. 14 shows the T2 maps acquired at different τ$_{180}$. The O2sat of the right ventricle (RV) and left ventricle (LV) measured by the gold standard method of invasive catheter sampling and blood gas analysis is indicated in parenthesis.

Estimation of the unknown parameters within the specified bounds revealed that the bound for T$_{2O}$ was active for six of the nineteen data sets, eleven sets for a and nine data sets for τ$_{ex}$. The O2sat values estimated by MRI ranged from 49% to 90%. The mean and standard deviation and range of the three nuisance parameters estimated from curve fitting of the L-M model were: 225.40±27.19 ms, (200-278.88 ms) for T$_{2O}$; 4.98±1.13 ms. (3.12-6 ms) for τ$_{ex}$; and 0.56±0.01 ppm, (0.52-0.57 ppm) for a.

Linear regression and Bland Altman plots comparing the proposed technique and predetermined calibration method against catheter based venous O2sat measurements are shown in FIGS. 13A-D. A significant linear relationship was observed for O2sat estimated using the proposed method with the reference blood gas measurement (y=1.02 x, R=0.998, p<0.001, 95% CI=0.99 to 1.05). The Bland Altman plot showed a low, non-significant bias of −1.4±4.0% (p=0.15, 95% CI=−3.32 to 0.55%) for venous O2sat estimated by the proposed technique. The limits of agreement were 6.5% and −9.2%.

One of the data sets, corresponding to an arterial O2sat of 100% and venous O2sat of 87% could not be used to determine O2sat from the predetermined calibration factors. In this data, the venous T2 (283.9 ms) was measured to be higher than the arterial T2 (274.1 ms). Of the remaining eighteen data sets analyzed, a significant linear relationship was seen for the calibration factor K=25 s$^{-1}$ (y=1.09x, R=0.996, p<0.001, 95% CI=1.05 to 1.14). The 95% CI indicates that the slope was significantly different from 1 for K=25 s$^{-1}$, but not for the method disclosed in this invention. The Bland Altman plots also revealed a significant bias for K=25 s$^{-1}$ (−6.8±5.7%, p=0.0001, 95% CI=−9.6 to −3.9%). The limits of agreement for the predetermined calibration method were larger than the technique in this disclosure (−18.0% to 4.4% for K=25 s$^{-1}$).

Conclusions from Animal Hypoxemia Experiment

A method to non-invasively determine blood oxygen saturation using quantitative T2 maps has been described and validated against invasive blood gas analysis across a range of oxygen saturation levels in a porcine model of progressive hypoxemia. The range of venous O2sat examined in this study covered the normal and abnormal levels seen with cardiovascular disease. O2sat estimated by the proposed MRI method demonstrated a very good agreement with invasive blood gas analysis. This novel approach obviates the need for patient-specific in vitro calibration, and provides auto-calibrated estimation of venous oxygen saturation by MRI.

The dependence of blood T2 on the inter-echo spacing in the CPMG pulse train was exploited to acquire a range of effective T2 values as a function of τ$_{180}$ and thereby generated sufficient data to perform a reliable fit of the four unknown parameters of the L-M model. In this example embodiment, these multiple estimates of blood T2 have been acquired using single-shot, T2-prepared, SSFP quantitative T2 maps of the ventricular blood pools. The T2 maps were acquired in a free breathing state, with the intention of designing and implementing a protocol that would be feasible in cardiovascular patients, many of whom have difficulty holding their breath.

The range of τ$_{180}$ times were chosen such that a reasonable tradeoff between sensitivity to oxygen saturation and insensitivity to flow induced dephasing was achieved. As seen in FIG. 1, the sensitivity to O2sat increases with increasing τ$_{180}$. However, moving protons undergo greater irreversible dephasing during the longer refocusing intervals, leading to increased sensitivity to flow and associated signal loss. It may be possible to rely on statistical sensitivity analysis to further optimize the range and sampling of τ$_{180}$.

In the interest of overall image acquisition time and practical application in the clinic, the example embodiment in the present disclosure utilizes the relatively simple model described in Eq. 1 to demonstrate the proposed solution for MR oximetry. The same methodology presented here could be used to estimate the parameters of more complex models.

Besides providing non-invasive access to virtually any location in the cardiovascular system, this MRI-based method also offers the ability to assess average O2sat over large regions of interest. Cather-based blood sampling in chambers where sufficient mixing has not occurred may result in inaccurate O2sat measurements as a small, localized sample is obtained. Non-invasive measurement of O2sat by MRI, on the other hand, allows the spatial averaging of O2sat within a large region of interest within cardiac chambers or blood vessels. This provides effective "mixing" of the blood within the image plane and thus may overcome one limitation of diagnostic invasive catheterization. In the future, three-dimensional imaging techniques may be developed to provide full spatial coverage of cardiac chambers and large vessels.

Fitting the L-M model by a constrained non-linear least squares in the animal experiment described here showed the activation of bounds for the nuisance parameters, which implies that the solution, up to some degree, was influenced by the selection of the bounds and not just the data. However, the selection of bounds was not subjective and was completely data driven; it is conjectured that these bounds will generalize to a broader population at least within a species. Even in cases where these bounds may become suboptimal, employing bounds provides more flexibility and reliance on measured data over using fixed, generic values for the unknown parameters.

Alternative Methodologies

Exchange Model/Imaging Sequence

MR oximetry techniques have been previously described to estimate blood oxygen saturation in the pediatric and adult population. However, these methods have not gained clinical acceptance and this may be due to the need for technique-specific and patient-specific in vitro calibration procedures. While other studies have performed T2 measurements across a range of $\tau_{180}$, the goal of these experiments was primarily to derive predetermined calibration parameters for the estimation of O2sat from a single T2 measurement. The technique presented in this disclosure is universal and would be applicable for any mathematical representation of the exchange/diffusion model that describes the dependence of blood T2 to its corresponding O2sat as a function of the inter-echo spacing ($\tau_{180}$). The data could therefore, potentially be acquired with any imaging sequence that achieves T2 weighting with a train of refocusing pulses. This technique would be especially valuable in patients, who may present under different hemodynamic and metabolic states and altered blood magnetic properties than the normal population.

Exploration with Four Equations

In Eq. (1) examined in the present disclosure, there are four unknowns.

Therefore, a minimum of four equations are required to estimate the four unknown parameters from the L-M model. In an example embodiment, the animal hypoxemia data sets were evaluated to estimate venous O2 sat using only T2 maps acquired at two different $\tau_{180}$ times of 12 and 20 ms. This provided two equations of venous and arterial blood each from these two T2 maps. The correlation graph shown in FIG. 11 demonstrates a good agreement between venous O2 sat measured by the technique disclosed in this invention when compared to the gold standard method of invasive catheter sampling and blood gas analysis.

Estimation of Venous O2 Sat from T2 Prepared Source Images

To illustrate the example embodiment described in (202, 208), an alternative form of the T2 map was acquired during the animal hypoxemia experiment, in which a constant number of 8 refocusing pulses was implemented across the different TE times in the T2 prepared source images. The resulting T2 prepared images, therefore, had varying $\tau_{180}$ times (TE=T2p×$\tau_{180}$). The signal measured in the blood from the source images were then used to estimate venous O2 sat using the method described in (202, 208). The correlation graph shown in FIG. 12 demonstrates a good agreement between venous O2 sat estimated by MRI and the gold standard method of invasive catheter sampling and blood gas analysis.

Six-Parameter Model

As another example embodiment, the performance of the calibration-free approach was evaluated with the more comprehensive model defined in Eq. (5). The terms in Eq. (5) were regrouped as:

$$R_{2b} = R_{2p'} + \qquad (6)$$
$$Hct(1-Hct)K\beta^2 + [\Delta kHct + 2\alpha\beta KHct(1-Hct)]\left(1 - \frac{\% SbO_2}{100}\right) +$$
$$\alpha^2 KHct(1-Hct)\left(1 - \frac{\% SbO_2}{100}\right)^2,$$

-continued where $$K = \tau_{ex}\omega_0^2\left(1 - \frac{2\tau_{ex}}{\tau_{180}}\tanh\frac{\tau_{180}}{2\tau_{ex}}\right).$$

Figure 15:
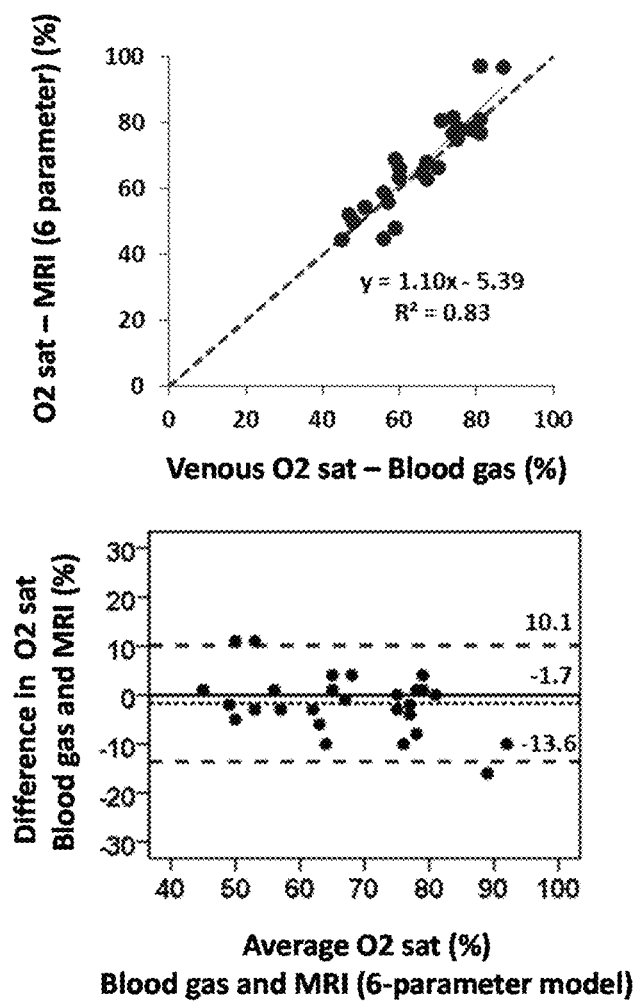
FIG. 15 illustrates the correlation and Bland Altman plots from the evaluation of the animal data, using a comprehensive L-M model described in Eq. 6, as an example embodiment.

The initial constraints are estimate and bounds constraints for the six unknown parameters in this model were: 0.70 [0,1] for venous O2sat, 0.004 [0.002,0.005] ms$^{-1}$ for $R_{2p'}$, 3[1,8] ms for $\tau_{ex}$, 0.2 [0.1, 0.4] ppm for $\alpha$, 0.06[0.02, 0.1] ppm for $\beta$, and 0.003[0.001,0.02] ms$^{-1}$ for $\Delta k$. FIG. 15 shows the correlation and Bland Altman Plots for the animal hypoxemia data. The results show that the technique presented in this disclosure is applicable to even more comprehensive models that relate T2 to O2sat.

Exploration without Using a Reference Measurement

In another example embodiment, the technique in the present disclosure was also evaluated without the use of an arterial T2 and O2sat reference measurement to estimate venous O2sat. The four venous T2 measurements at $\tau_{180}$ times of 12, 15, 20 and 25 ms were evaluated together with the hematocrit.

The venous O2sat estimated using the four equations of venous T2 alone ranged from 26% to 74%. FIGS. 16A-B show the regression and Bland Altman plots comparing the estimated venous O2sat against invasive catheter O2sat measurements. The results show that the technique presented in this disclosure may be applied even without the use of a reference blood T2 and O2sat measurement.

Testing in a Cohort of Patients

The technique described in this disclosure was further evaluated in a cohort of nine patients with cardiovascular disease. The patients (age 51.44±19.66 years, four females) were clinically indicated for invasive right heart catheterization and cardiac MRI. Four short-axis T2 maps including both arterial (left ventricle, LV) and venous (right ventricle, RV) blood were acquired at $\tau_{180}$=12, 15, 20 and 25 ms respectively at 1.5 T. The resulting eight blood T2 measurements (four venous and four arterial), non-invasive arterial O2sat obtained with a pulse oximeter (SpO2), and hematocrit on the day of MRI, were jointly processed to fit the L-M model using the approach described above. Venous O2sat was then compared against the invasive reference measurement.

Results

Example T2 maps acquired in one patient are shown in FIG. 17, which shows the venous T2 values of the right ventricle in the upper left and the arterial T2 values of the left ventricle in the lower right of each T2 map. The time between MRI and invasive measurements ranged from four hours to one week. The average hematocrit levels were 40.34±6.56% (range, 30.7%-48.4%). Figure x shows the comparison of venous O2sat estimated from MRI against the invasive measurement for each patient; the mean values of the estimated nuisance parameters were: $T_{2O}$ (mean: 249.95±20.05 ms, range: 214.39-272.58 ms), $\tau_{ex}$ (mean: 3.65±1.55 ms, range: 2.12-6.83 ms) and a (mean: 0.49±0.11 ppm, range: 0.27-0.6 ppm). The average absolute mean difference between the MRI and invasive O2sat measurements was 4.44±3.24% (range, 1% to 11%). A paired t-test between the two measurements showed no statistically significant difference (p=0.29).

The result of this preliminary evaluation in patients by direct comparison against invasive O2sat measurements is promising and demonstrates good agreement with the gold standard measurement of invasive catheterization.

CONCLUSION

Thus, in view of the disclosure above, a novel method to non-invasively determine oxygen saturation has been developed. The proposed solution for non-invasive estimation of blood O2sat in the heart was implemented and validated across a range of physiological and pathological O2sat levels in healthy volunteers, animals and cardiovascular patients. In this example embodiment, effective T2 measurements of arterial and venous blood using quantitative T2 prepared SSFP quantitative T2 maps were acquired at distinct inter-echo spacings and fit to the L-M model to non-invasively estimate O2sat and other nuisance parameters. The estimation of venous O2sat from these effective T2 measurements of the blood pool were in good agreement with the reference measurement obtained by invasive catheterization. An evaluation of the previously proposed method of applying a predetermined calibration factor to a simplified L-M model was also used to estimate venous O2sat; the results show greater bias and larger variability compared to the proposed calibration-free oximetry method.

What is claimed:

1. A method for determining oxygen saturation (O2sat) of blood using magnetic resonance (MR) image data, comprising:
   acquiring multiple transverse relaxation time (T2) prepared source images, each of the source images having distinct pulse timing between refocusing pulses ($\tau_{180}$);
   deriving multiple T2-measurements from the T2 prepared source images, wherein each T2 measurement is derived from a combination of source images all having the same $\tau_{180}$ and different number of refocusing pulses (n);
   using the multiple measurements of blood T2 ($T_{2b}$) within a same blood pool, wherein each blood T2 measurement generated using source images with unique $\tau_{180}$, yields one Luz-Meiboom model derived equation of the form:

$$\left(1 - \frac{\% SbO_2}{100}\right)^2 = \frac{\left(\frac{1}{T_{2b}} - \frac{1}{T_{2O}}\right)}{(Hct)(1-Hct)\tau_{ex}(\alpha\omega_0)^2\left(1 - \frac{2\tau_{ex}}{\tau_{180}}\tanh\left(\frac{\tau_{180}}{2\tau_{ex}}\right)\right)}$$

taking T2b together with independent measurements of patient hematocrit (Hct); and together with $\omega_0$, the proton resonance frequency that is fixed for the static magnetic field strength at which the measurements are acquired; and
   applying a non-linear curve fitting to a system of equations generated using multiple T2-measurements of a blood pool, each with a unique $\tau_{180}$, to determine all of the unknown model parameters uniquely in each patient,
   wherein the unknown model parameters include at least one of % $SbO_2$, $T_{2O}$, $T_{ex}$ and $\alpha$,
   wherein % $SbO_2$ is the unknown blood O2sat in the system of equations that correspond to the blood pool whose O2sat needs to be determined,
   $T_{2O}$ is the T2 value of fully oxygenated blood, and
   $\tau_{ex}$ is the water proton exchange time between erythrocytes and plasma, and
   $\alpha$ is a dimensionless parameter dependent on the susceptibility difference of deoxy- and oxyhemoglobin in blood.

2. The method of claim 1, further comprising:
   receiving electrocardiogram data from a patient under examination; and
   triggering the acquiring of the T2 prepared source images using the electrocardiogram data.

3. The method of claim 1, wherein ranges or probabilistic priors are enforced, during curve fitting, on the unknown quantities in the L-M model, the method further comprising:
   constraining allowed ranges of at least one of % $SbO_2$, $T_{2O}$, $T_{ex}$, and $\alpha$; and
   estimating the unknown quantities in accordance with the constraining.

4. The method of claim 1, the deriving multiple T2-maps further comprising generating single slice maps in which a pixel value reflects T2 of blood in chambers of a heart and blood vessels of a patient from whom the T2 prepared source images were acquired.

5. The method of claim 1, further comprising:
   using a non-invasive arterial oxygen saturation (O2 sat, % $SbO_2$) measurement, measured using non-invasive pulse oximetry during the acquisition of MR data, that corresponds to blood T2 measurements in an arterial blood pool, to create an arterial reference system of equations that are jointly processed with the system of venous (or blood pool whose O2sat is unknown) blood T2 equations to aid in the non-linear curve fitting to determine the unknown quantities of the L-M model.

6. The method of claim 1, further comprising:
   estimating the unknown O2sat for a blood pool with the system of blood T2 equations corresponding to the blood pool alone without the need for an arterial reference system of equations.

7. The method of claim 1, wherein to aid with each blood T2 measurement, an MR image, containing the blood pool, is collected without T2 preparation (0 refocusing pulses).

8. A method for determining oxygen saturation (O2sat) of blood using magnetic resonance (MR) image data, comprising:
   obtaining multiple transverse relaxation time (T2) prepared source images, each of the T2 source images having distinct pulse timing ($\tau_{180}$) and number of refocusing pulses (n);
   directly using a measured signal, S, an MR signal for a given blood pool in the multiple T2 prepared source images to yield
   a Luz-Meiboom (L-M) model derived equation of the form:

$$\left(1 - \frac{\% SbO_2}{100}\right)^2 = \frac{\left(\frac{\ln\left(\frac{S}{S_0}\right)}{-n\tau_{180}} - \frac{1}{T_{2O}}\right)}{(Hct)(1-Hct)\tau_{ex}(\alpha\omega_0)^2\left(1 - \frac{2\tau_{ex}}{\tau_{180}}\tanh\left(\frac{\tau_{180}}{2\tau_{ex}}\right)\right)};$$

taking S together with independent measurements of patient hematocrit (Hct) and $\omega_0$, the proton resonance frequency that is fixed for the static magnetic field strength at which the measurements are acquired; and
   applying a non-linear curve fitting to a system of equations generated from the multiple T2 prepared source images, each with a unique $\tau_{180}$, to determine all of the unknown model parameters uniquely in each patient, wherein the unknown model parameters include at least one of % $SbO_2$, $T_{2O}$, $\tau_{ex}$, $\alpha$, and $S_0$, wherein % $SbO_2$ is the unknown blood O2sat in the set of equations that correspond to venous blood or blood pool whose O2sat needs to be determined, $T_{2O}$ is the T2 value of fully oxygenated blood, $\tau_{ex}$ is the water proton exchange time between erythrocytes and plasma, $\alpha$ is a dimensionless parameter dependent on the susceptibility difference of deoxy- and oxyhemoglobin, and $S_0$ is the steady-state MR signal.

9. The method of claim 8, further comprising:
receiving electrocardiogram data from a patient under examination; and
triggering the acquiring of the T2 prepared source images using the electrocardiogram data.

10. The method of claim 8, wherein ranges or probabilistic priors are enforced, during curve fitting, on the unknown quantities in the L-M model, the method further comprising:
constraining allowed ranges of at least one of % $SbO_2$, $T_{2O}$, $T_{ex}$, $\alpha$ and $S_0$; and
estimating the unknown quantities in accordance with the constraining.

11. The method of claim 8, further comprising:
using a non-invasive arterial oxygen saturation (O2 sat, % $SbO_2$) measurement, measured using non-invasive pulse oximetry during the acquisition of MR data, that corresponds to the arterial blood signal, S, in the T2 prepared source images, to create an arterial reference system of equations that are jointly processed with the system of venous (or blood pool whose O2sat is unknown) blood MR signal equations to aid in the non-linear curve fitting to determine the unknown quantities of the L-M model.

12. The method of claim 8, further comprising:
estimating the unknown O2sat for a blood pool with the system of T2 prepared blood MR signal equations corresponding to the blood pool alone without the need for an arterial reference system of equations.

13. The method of claim 8, wherein each T2 prepared source image is generated using a distinct combination of n and $\tau_{180}$, wherein n is the number of refocusing pulses.

14. The method of claim 8, wherein constraints are imposed on n and $\tau_{180}$ to limit signal dephasing effects that may affect accuracy, wherein n is the number of refocusing pulses.

15. The method of claim 8, wherein to aid with the curve fitting, an MR image, containing the blood pool, is collected without T2 preparation (0 refocusing pulses).

16. The method of claim 15, wherein $S_0$ is equated to the measured signal S of the blood pool within an MR image collected without any T2 preparation.

17. The method of claim 15, wherein the measured signal S of the blood pool within an MR image collected without T2 preparation, is used to initialize the constraints for $S_0$.

* * * * *